United States Patent
Lau et al.

[11] Patent Number: 5,492,648
[45] Date of Patent: Feb. 20, 1996

[54] ORGANIC OIL STABILIZATION TECHNIQUES

[76] Inventors: John R. Lau, 585 King Beach Dr., Howard, Ohio 43028; Bruce K. Schrier, 1635 Linwood Dr., Wooster, Ohio 44691

[21] Appl. No.: 84,973

[22] Filed: Jul. 2, 1993

[51] Int. Cl.$^6$ .............. B01J 13/00; A01N 25/00; A23L 1/222; A61K 7/46
[52] U.S. Cl. ............. 252/312; 252/314; 424/405; 426/651; 426/662; 512/2; 514/941
[58] Field of Search .................... 252/312, 314; 514/941; 426/662, 651; 424/405; 512/2

[56] References Cited

U.S. PATENT DOCUMENTS

| | | | |
|---|---|---|---|
| 2,977,283 | 3/1961 | Meyer et al. | 514/941 |
| 3,282,705 | 11/1966 | Hansen | 252/312 X |
| 4,218,221 | 8/1980 | Cottell | 252/314 X |
| 4,252,827 | 2/1981 | Yokoyama et al. | 514/941 |
| 4,285,981 | 8/1981 | Todd, Jr. et al. | 426/662 X |
| 4,621,023 | 11/1986 | Redziniak et al. | 252/312 X |
| 4,966,779 | 10/1990 | Kirk | 252/312 X |
| 5,114,703 | 5/1992 | Wolf et al. | 514/941 |
| 5,152,923 | 10/1992 | Weder et al. | 252/312 |
| 5,162,377 | 11/1992 | Kakoki et al. | 541/941 |

*Primary Examiner*—Richard D. Lovering
*Attorney, Agent, or Firm*—Frijouf, Rust & Pyle

[57] ABSTRACT

High impact energy is applied to a modified lecithin in water, to form a base product. A block copolymer surfactant, water and organic oil are added to this base product, and high impact energy is applied once again. The resultant product is a stable aqueous distribution of the organic oil.

1 Claim, No Drawings

ORGANIC OIL STABILIZATION TECHNIQUES

DEFINITIONS

LECITHIN: Lecithin is a lipid, the best commercial source of which is plant phosphatides. Soy beans are presently the primary large scale source of lecithin. An exhaustive supply of information about lecithin is obtainable from Central Soya Company, Fort Wayne, Ind., U.S.A. For further information, see U.S. Pat. No. 4,126,591.

MODIFIED LECITHIN: Modified Lecithins are available from the Archer Daniels Midland Company, Box 1470 Decatur, Ill. 62525 and other commercial sources. Hydroxylated and acetylated, hydroxylated, and sulphonated lecithins are useful forms known in the marketplace. The hydroxylated form is preferred in this invention.

ORGANIC COMPOUNDS: As used herein, "organic compounds" means water-insoluble or sparingly soluble compounds or mixtures of the same which are used in food stuffs and in consumer products. Perfume and other fragrances, skin care and skin use products such as moisturizers and insect repellents are examples. Also among these organic compounds are flavor oils, and vegetable oils such as corn oil and canola oil as special categories. Included are solids that may become oils at higher temperatures, such as menthol.

BLOCK COPOLYMER SURFACTANTS: One type of surfactant used herein is a polyoxyethylene polyoxypropylene copolymer with an average molecular weight of 4.4 kD. Polyoxypropylene is the hydrophobic portion, comprising 20% to 90%, by weight, of the final molecule. Polyoxyethylene is the hydrophilic group which constitutes 10% to 80% of the final molecular weight of the molecule. Another type of surfactant used herein is the same as the type described, but having a molecular weight of 12.6 kD. These two surfactants are of a class of surfactants known generally as block copolymer surfactants. One source of these surfactants is BASF Corporation, Chemicals Division, 100 Cherry Hill Road, Parsippany, N.J. 07054.

CAVITATION ENERGY/HIGH-ENERGY INPUT: Microfluidization or sonication, for example, or other similar high-energy applications, produce cavitation.

PREAMBLE

Throughout this disclosure, an effort is made to convey the novel result of very small droplets of hydrophilic liquids being distributed throughout a liquid phase. Specifically, hydrophobic molecules such as oil in water.

"Emulsion" has a very well recognized physical status. The limitations of oil emulsification and water is well known. This invention is not an emulsion; it is superior to an emulsion.

Some refer to the physical state of oil and water according to this invention as a nanodispersion. This term is not as widely known as the term "emulsion" but is known. This invention is not accurately limited to the title of nanodispersion. It is not a mere dispersion, but its structure at the molecular level has not been determined.

The specification disclosure of this invention will delineate the true nature of this invention without need for defining titles; which, as hereto are commonly defined as "emulsion" or "dispersion", are insufficiently accurate for the molecular distribution and high concentration achieved by the invention herein.

FIELD OF THE INVENTION

This invention relates to the stabilization of aqueous dispersions of organic materials.

BACKGROUND OF THE INVENTION

Achieving stability of organic oils in aqueous products such as beverages, colognes and perfumes, paints, organic pesticides, cosmetics and other skin-care products, certain pharmaceuticals, and other oil based products, has long been a challenge to manufacturers.

Achieving this stability has been a goal for manufacturers of edible products, because of the necessity to avoid organic solvents in products such as beverages or foods. The beverage industry, for example, has an intense need for stable aqueous dispersions of organic compounds. Their dispersions must withstand high dilution, long storage, carbonation, and wide temperature variations. The instability caused by these factors usually results in either ringing or settling of the organics in the beverage. Consumers find these results unappealing, as beverages so affected are less than optimally attractive and provide uneven taste.

Accordingly, the beverage flavor industry has developed emulsion systems which are combinations of materials used to raise the specific gravity of the organic oil, and which use natural and synthetic surfactants as emulsifiers. Raising the oil's specific gravity promotes improved stability and more even dispersion of the oil in an aqueous medium. The most commonly used material for this purpose is brominated vegetable oils ("BVO"). Gum arabic is the most commonly employed emulsifier. Due to toxicity concerns, some governments have severely limited the use of BVOs in beverages to a concentration far lower than what is necessary to achieve stability of the flavor oil. Industry chemists have searched fruitlessly for an acceptable BVO substitute. The closest viable substitute has been ester gum. Substitution of ester gum for most of the BVO, however, has not produced reliably stable emulsions.

Replacements for ester gum, such as synthetic gums, other natural gums, and modified food starches, have also failed to produce reliably stable emulsions.

Because of these instability problems, flavor oil manufacturers can only ship concentrations of up to around 5% to 8% oil (w/w in water) to bottlers. Beyond this concentration range, the limits of stability and viscosity are breached, and the oil separates into phases.

One of the most informative dissertations on this organic oil stability problem remains "Manufacture and Analysis of Carbonated Beverages", by Morris B. Jacobs, PhD., Chemical Publishing Co., Inc., NY, N.Y. (1956). Teaching on the subject has not advanced significantly since his work.

It is an object of this invention to provide a formulation and formulating system which can provide stable, high-concentration aqueous dispersions for a large variety of organic compounds. It has been discovered, according to this invention, that organic solvents for organic materials in aqueous media are replaced by a combination of stabilizing agents that are non-toxic and, when mixed in the right proportions, provide remarkably higher concentrations of organic oils in aqueous media.

SUMMARY OF PREFERRED EMBODIMENT OF THE INVENTION

A modified lecithin in a water-based environment producing structure of the modified lecithin such that, when mixed with a block copolymer surfactant and water-insoluble organic compounds and impacted with high energy, the organic compounds are incorporated into the mixture at heretofore unattainable high concentrations and 5remain physically stable for long periods of time.

DETAILED DESCRIPTION

The invention will now be illustrated by specific examples in order that those skilled in this technology may better understand the practice of the invention. The invention is, of course, not limited to these specific examples, but also includes all the features and advantages described above.

EXAMPLE 1

Best mode example for flavorant oils and other organic oils:

200 grams of hydroxylated lecithin is homogenized in 800 ml of distilled water. This homogenate is subjected to three microfluidization steps at about 40 psi head pressure, to assure a very fine dispersion. The resultant "base product", a 20% stock of hydroxylated lecithin, is stored at 4° C. until used. As used in this Example, and throughout this disclosure, this modified lecithin stock product is referred to as "base product". 200 grams of block copolymer surfactant is suspended in 800 ml of cold distilled water and subjected to overnight mixing on a magnetic mixer at 4° C. to form a 20% stock. The preferred copolymer is F-127 and selected from the class of surfactant generally known as block copolymer surfactants. L-121; another copolymer from this class, may also be used.

For subsequent preparation of organic oil concentrates using these two stocks, 200 ml of the base product and 250 ml of 20% block copolymer surfactant are homogenized together with about 160 grams of orange oil and sufficient water to achieve a final homogenate volume of 1000 ml. This homogenate is microfluidized at 20 psi head pressure to obtain the final organic oil distribution, which is a stable oil concentrate containing 16% (w/w) flavorant.

Supporting evidence in trial studies indicates that the 16% (w/w) flavorant is the preferred embodiment, but a range of up to 23% (w/w) is possible. The best mode is also the preferred embodiment. Limits are due to viscosity, not instability. The lower useful limit is about 1%.

EXAMPLE 2

A. Modified lecithin is homogenized with water to form a base product.

B. To the base product of Step (A) is added by mixing (usually by homogenization), about 0.2–0.3-fold (by weight) surfactant such as F-127 br L-121, 0.6–1.33-fold (by weight) of flavor oil and water. These components are together exposed to high-energy input whereby the oil is thus stably distributed for an extended time (more than 4 months), which exceeds the industry's normal stability standards.

EXAMPLE 3

The same steps are taken as in Example 1, above, except 150 ml. of base product, 187.5 ml. of 20% F-127 surfactant, and 200 grams of orange oil, with water, yield a 1000 ml homogenate. These together are microfluidized to produce about a 20% (w/w) flavorant oil concentrate, which exceeds the industry's present concentrations.

EXAMPLE 4

A fragrance oil concentrate is produced by mixing 100 ml. of the base product, 2.5 ml of L-121, 80 grams of a spice fragrance oil, and water. These together are homogenized then microfluidized to produce at least an 8% (w/w) fragrance distribution.

EXAMPLE 5

The same steps can be taken as in Example 4, above, except 125 ml of 20% stock of F-1.27 is substituted in place of L-121, to yield an 8% (w/w) fragrance oil distribution.

EXAMPLE 6

The same steps can be taken as in Example 3, above, except 20% homogenate of hydroxylated lecithin is used without first being microfluidized.

EXAMPLE 7

250 ml. of base product are mixed with 300 ml. of 20% F-127 surfactant, 200 grams of lemon-lime flavor oil, and water, then microfluidized together to yield a stable flavor oil distribution.

EXAMPLE 8

The same steps are taken as in Example 4, above, except N,N-Diethyl-m-toluamide ("DEET") in a range from about 130 grams to 250 grams is substituted for fragrance oil to produce a 13% to 25% insect repellent.

EXAMPLE 9

4,558 ml N,N-Diethyl-m-toluamide ("DEET") insect repellent are mixed with 471 ml of L-121 surfactant. To the resultant homogenate is added 1,816 ml. of base product, and 0.01% pyridinethione. These are mixed together by use of a low-speed mixer. During mixing, 11,350 ml deionized water are added to the mix. The resultant mix is then mixed at high speed for 15 minutes. The solution is then microfluidized at about 60 psi head pressure and about 7,400 psi shear pressure. The entire solution is again microfluidized just long enough to expel a volume of about 1 L. This expelled volume is returned to the reservoir, DEET and the entire volume (18.195 L) is then microfluidized to produce a 25% insect repellent. A sample is taken therefrom for particle size measurement and stability tests.

EXAMPLE 10

Lemon flavor (citral) concentrate is made by homogenizing together 200 ml of base product, 250 ml of a 2{)% of stock of F-127 and 160g of citral with sufficient water to make a volume of 1 L. This mixture is then microfluidized to achieve a stable 16% (w/w) flavor distribution with a mean particle diameter of about 67 nm.

EXAMPLE 11

Insect repellent is prepared as in Example 9, except that a 20% stock of acetylated and hydroxylated lecithin is substituted for the base product.

EXAMPLE 12

For some applications, depending on the organic oil to be distributed, other block copolymers may be substituted for the F-127 or L-121.

EXAMPLE 13

In the process of Example 1, the final microfluidization of the mixture concentrate may be substituted by two or more passes through a high pressure (10,000 psi) homogenizer (such as the homogenizer made by Union Pump Co. of North Andover, Mass.).

EXAMPLE 14

A butter flavor concentrate is prepared by homogenizing together 200 ml of base product, 250 ml of 20% stock of F-127, and 160 g of liquid butter flavor with sufficient water to make a volume of 1 L. This mixture is then microfluidized to achieve a stable 16% (w/w) flavor distribution with a mean particle diameter of about 35 nm.

The above examples are drawn from actual experiments. Those skilled in the art will recognize that other stable, high concentrations of organics may be prepared in like manner. Every possible ratio and order of procedure based on these experiments may not be stated herein, but will be within the ability of those skilled in the art.

It should be noted that "organic oil" may be two or more components. Those given herein are for teaching purposes, and it should be further noted that variations in the type of oil used require concomitant variations in base product; surfactant and cavitation energy.

Once the foregoing examples are understood, it should be well within the ability of one skilled in the art to modify the quantities of these examples with routine manipulation of base product, surfactant, cavitation energy and organic oil.

The disclosure herein is represented as a fully enabling teaching, and the above examples show the best mode for using the invention.

What is claimed is:

1. A product of organic oil distributed throughout a body of hydroxylated lecithin in a water continuous phase, made by the process steps of:

(1) applying cavitation energy to a mixture of hydroxylated lecithin in water;

(2) adding a block copolymer surfactant and subject organic oil to the resultant of (1) and again applying cavitation energy.

\* \* \* \* \*